(12) United States Patent
Bobo, Sr.

(10) Patent No.: US 7,654,967 B2
(45) Date of Patent: Feb. 2, 2010

(54) GAS COLUMN PRESSURE MONITORING DEVICE

(75) Inventor: Donald E. Bobo, Sr., Fountain Valley, CA (US)

(73) Assignee: InnerSpace Medical, Inc., Santa Ana, CA (US)

(*) Notice: Subject to any disclaimer, the term of this patent is extended or adjusted under 35 U.S.C. 154(b) by 495 days.

(21) Appl. No.: 11/683,387

(22) Filed: Mar. 7, 2007

(65) Prior Publication Data

US 2007/0208270 A1    Sep. 6, 2007

Related U.S. Application Data

(62) Division of application No. 10/104,729, filed on Mar. 21, 2002, now abandoned.

(60) Provisional application No. 60/277,565, filed on Mar. 21, 2001.

(51) Int. Cl.
*A61B 5/00* (2006.01)
(52) U.S. Cl. .................................................... 600/561
(58) Field of Classification Search ................ 600/561, 600/486, 585, 587, 591, 509, 588; 73/708, 73/721, 746; 251/334; 604/246; 338/4, 338/39, 42; 285/80
See application file for complete search history.

(56) References Cited

U.S. PATENT DOCUMENTS

| 3,662,743 A | 5/1972 | Amarante et al. |
|---|---|---|
| 4,903,707 A | 2/1990 | Knute et al. |
| 4,934,475 A | 6/1990 | Urakami |
| 5,573,007 A | 11/1996 | Bobo, Sr. |
| 5,644,285 A | 7/1997 | Maurer |
| 5,984,879 A | 11/1999 | Wallace et al. |
| 6,231,524 B1 | 5/2001 | Wallace et al. |
| 6,447,462 B1 | 9/2002 | Wallace et al. |

*Primary Examiner*—Max Hindenburg
*Assistant Examiner*—Brian Szmal
(74) *Attorney, Agent, or Firm*—Inskeep IP Group, Inc.

(57) ABSTRACT

The present invention provides a device for efficiently coupling a pressure monitoring device to a pressure transducer. In addition, the present invention reduces or eliminates the likelihood air will be unintentionally injected into the pressure monitoring device while connecting the pressure monitoring device to a pressure transducer. In one embodiment, the present invention includes a pressure monitoring coupler comprising a sealing member and a device body. The sealing member comprises a sealing flange connected to an engagement member. The engagement member includes a first and second O-ring positioned thereon. The device body comprises a pressurizing lumen and an intersecting monitoring lumen in communication with a receiving aperture. During use, a pressure monitoring catheter is inserted into a patient's tissue. The pressure monitoring catheter and a transducer are connected to the device body of the present invention. Thereafter, the sealing member is inserted into the device body while the pressure within the pressure monitoring catheter is maintained at or less than a state or equilibrium with the pressure applied by the tissue.

11 Claims, 6 Drawing Sheets

GAS COLUMN PRESSURE MONITORING DEVICE

CROSS REFERENCE TO RELATED APPLICATIONS

The present invention is a divisional of U.S. patent application Ser. No. 10/104,729 filed Mar. 21, 2002 now abandoned entitled "Gas Column Pressure Monitoring Device," which claims benefit of U.S. Provisional Application Ser. No. 60/277,565, filed Mar. 21, 2001; and discloses subject matter related to U.S. Pat. No. 5,573,007, issued Nov. 12, 1996, entitled "Gas Column Pressure Monitoring Catheters," all of which are incorporated herein by reference.

BACKGROUND OF THE INVENTION

Presently, biologically compatible air-based pressure monitoring catheters are used in a number of medical applications to monitor pressure at various locations within a mammalian body. For example, air-based pressure monitoring catheters may be inserted into the skull of a patient thereby permitting the external monitoring of intra-cranial pressure.

Currently, a number of air-based pressure monitoring catheters have been developed. Generally, these air-based pressure monitoring catheters comprise a catheter having an air lumen formed therein which communicates with a bladder positioned at or near its distal end. In addition, the catheter includes a connector located at or near its proximal end which may be connected to an external pressure transducer. During use, the volume of the bladder attached to the catheter changes as pressure varies in accordance with Boyle's Law ($P_1 V_1 = P_2 V_2$). As a result, the pressure of the gas within the catheter becomes equal to that of the environment surrounding the bladder. The media surrounding the bladder must be capable of movement to accommodate the variations in bladder volume as pressure changes. As such, pressure monitoring within a flowable liquid media has not proven difficult as the media is capable of accommodating the variations in bladder volume. However, one shortcoming of currently available air-based pressure monitoring catheters becomes evident when used to measure the pressure within an enclosed space, such as when used to monitor intra-cranial pressure.

When used to monitor intra-cranial pressure the bladder may become over inflated as a result of the movement of the media. As a result, the bladder may exert excessive force on the surrounding brain tissue as the brain tissue continues to move in response to changes in the intra-cranial pressure. The brain tissue, positioned within the skull, has a limited ability to move in response to the changes in bladder volume. As a result, the continued exertion of excessive force by the bladder on the surrounding brain tissue could result in a stroke, brain damage, or death.

Similarly, the use of air-based pressure monitoring catheters in negatively pressurized environments has proven problematic. Typically, a deflated bladder will immediately inflate to a pressure equal to environment surrounding the bladder the when introduced into a negatively pressurized environment. During use, the bladder may be capped to isolate the bladder from the external environment thereby permitting the accurate monitoring of pressure within the body. Often excessive air may be unintentionally injected into the bladder while connecting the pressure monitoring device to a pressure transducer. As a result, the over inflated bladder may exert an excessive and detrimental force on the surrounding tissue.

Thus, in light of the foregoing, there is a ongoing need for a pressure monitoring connector capable of connecting a gas column pressure monitor to a pressure transducer.

BRIEF SUMMARY OF THE INVENTION

The present invention provides a device for efficiently coupling a pressure monitoring device to a pressure transducer. In addition, the present invention reduces or eliminates the likelihood air will be unintentionally injected into the pressure monitoring device while connecting the pressure monitoring device to a pressure transducer.

In one embodiment, the present invention includes a pressure monitoring coupler comprising a sealing member and a device body. The sealing member comprises a sealing flange connected to an engagement member. The engagement member includes a first and second O-ring positioned thereon. The device body comprises a pressurizing lumen and an intersecting monitoring lumen in communication with a receiving aperture.

During use, a pressure monitoring catheter is inserted into a patient's tissue. The pressure monitoring catheter and a transducer are connected to the device body of the present invention. Thereafter, the sealing member is inserted into the device body while the pressure within the pressure monitoring catheter is maintained at or less than a state or equilibrium with the pressure applied by the tissue.

Other objects, features, and advantages of the present invention will become apparent from a consideration of the following detailed description.

BRIEF DESCRIPTION OF THE DRAWINGS

The apparatus of the present invention will be explained in more detail by way of the accompanying drawings, wherein.

DETAILED DESCRIPTION OF THE INVENTION

Disclosed herein is a detailed description of various embodiments of the present invention. This description is not to be taken in a limiting sense, but is made merely for the purpose of illustrating the general principles of the invention. The overall organization of the detailed description is for the purpose of convenience only and is not intended to limit the present invention.

Figure 1:
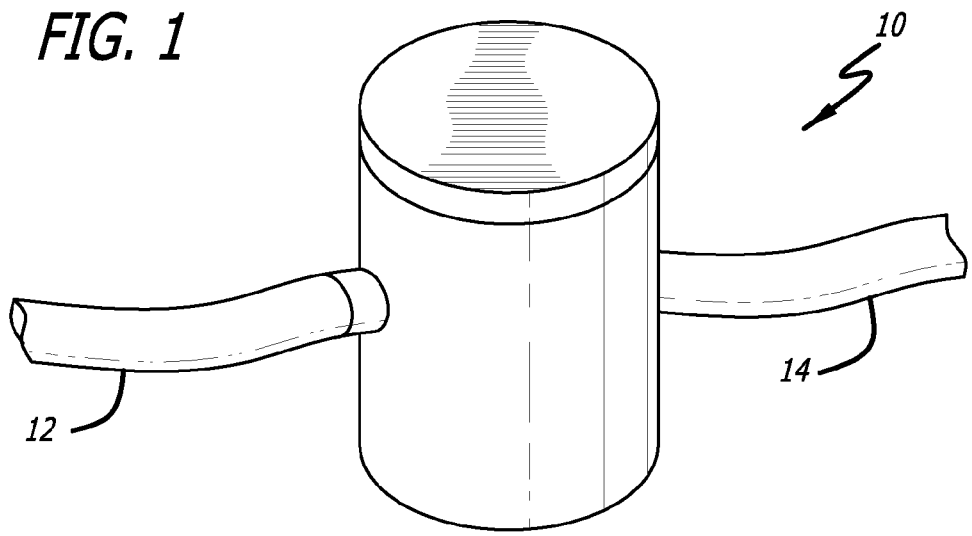
FIG. 1 shows a perspective view of the present invention.

FIG. 1 shows the pressure monitoring connector 10 of the present invention. As shown, pressure monitoring connector 10 is in communication with a catheter 12 and a transducer conduit 14. While the pressure monitoring device 12 of the present invention is designed for use with a variety of pressure monitoring devices used for monitoring the pressure within a mammalian body, it is particularly well suited for use with gas column pressure monitoring devices and catheters such as disclosed in U.S. Pat. No. 5,573,007, issued Nov. 12, 1996, entitled "Gas Column Pressure Monitoring Catheters" which is hereby incorporated by reference in its entirety as if fully set forth herein. As those skilled in the art will appreciate, the exemplary pressure monitoring device disclosed herein is designed to prevent or minimize trauma to the patient while providing the user with accurate information regarding the internal pressure at a selected location of the patient's body. While the pressure monitoring device of the present invention may be used in conjunction with of pressure monitoring devices to monitor the pressure at locations throughout the patient's body, it is particularly useful in negative pressure environments or within confined spaces. For example, the pressure monitoring device of the present invention may be used to monitor intra-cranial pressure or pressure within the vena cava.

Figure 2:
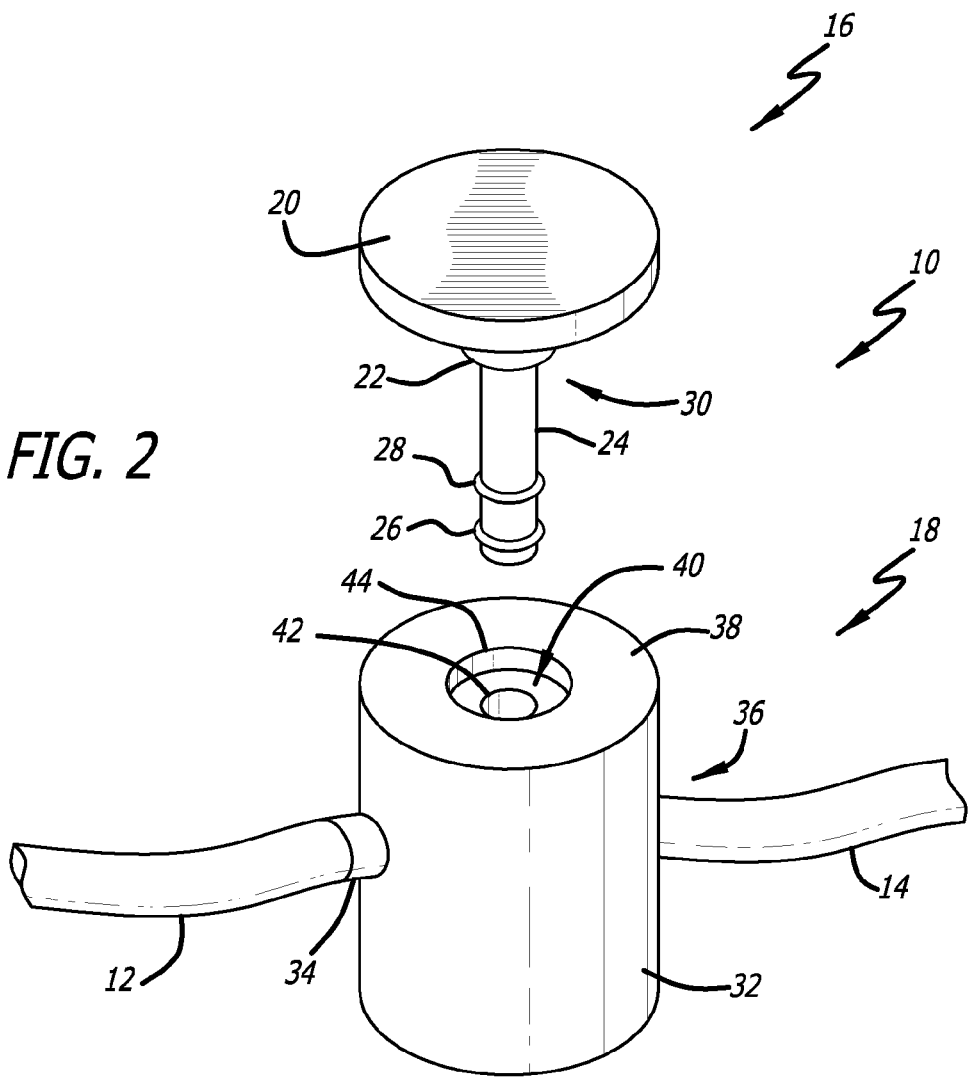
FIG. 2 shows a perspective view of the present invention wherein the sealing member is displaced from the device body.
Figure 3:
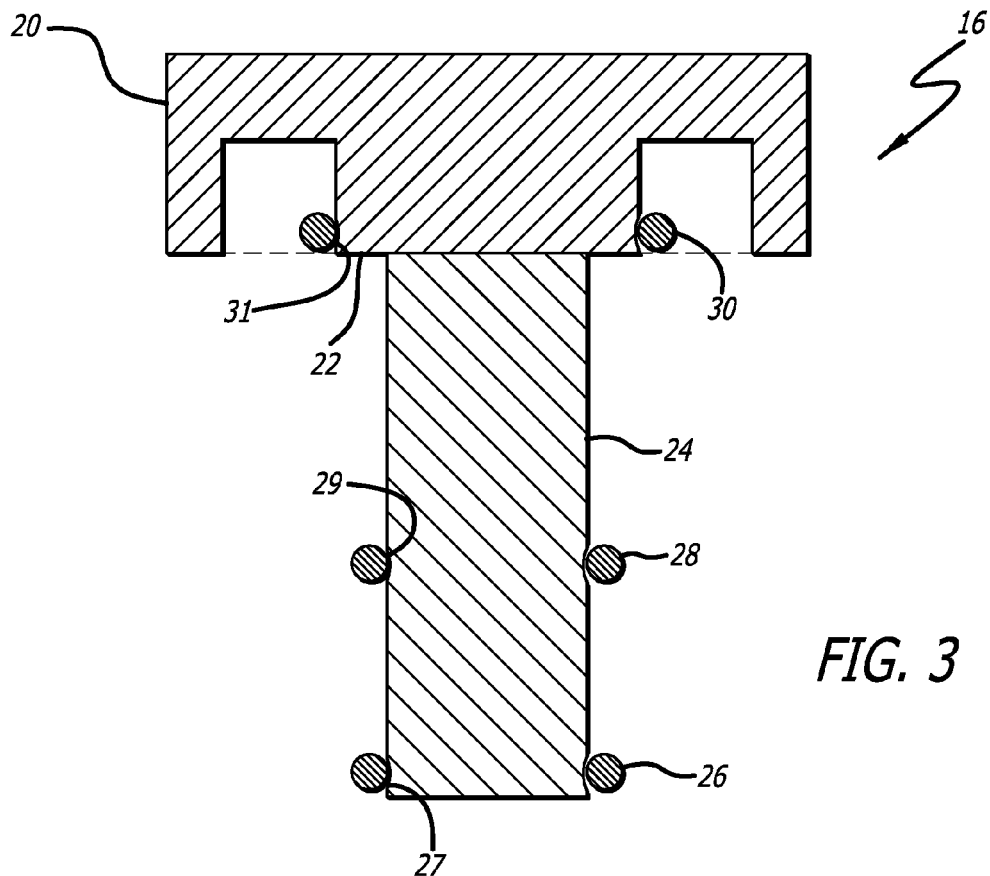
FIG. 3 shows a cross-sectional view of the sealing member of the present invention.

FIG. 2 shows the pressure monitoring connector 10 of the present invention. As shown, the monitoring device 10 of the present invention comprises a sealing member 16 capable of engaging a device body 18. As shown in FIGS. 2 and 3, the sealing member 16 comprises a surface 20 having a sealing flange 22 located or otherwise formed thereon. The sealing flange 22 is coupled to an engagement member 24. A first O-ring 26 and a second O-ring 28 are positioned on the engagement member 24. In one alternate embodiment, the engagement member 24 may include a first O-ring channel 27 capable of receiving the first O-ring 26 therein, and a second O-ring channel 29 capable of receiving the second O-ring 28 therein. A sealing O-ring 30 may be positioned on or proximate to the sealing flange 22. Like the engagement member 24, the sealing flange 22 may include a sealing O-ring channel 31 capable of receiving the sealing O-ring 30 therein. Those skilled in the art will appreciate that the first and second O-rings 26, 28, respectively, or the sealing O-ring 30 may attached to the engagement member 24 or the sealing flange 22 in a variety of ways, including adhesively attached or mechanically attached.

Figure 4:
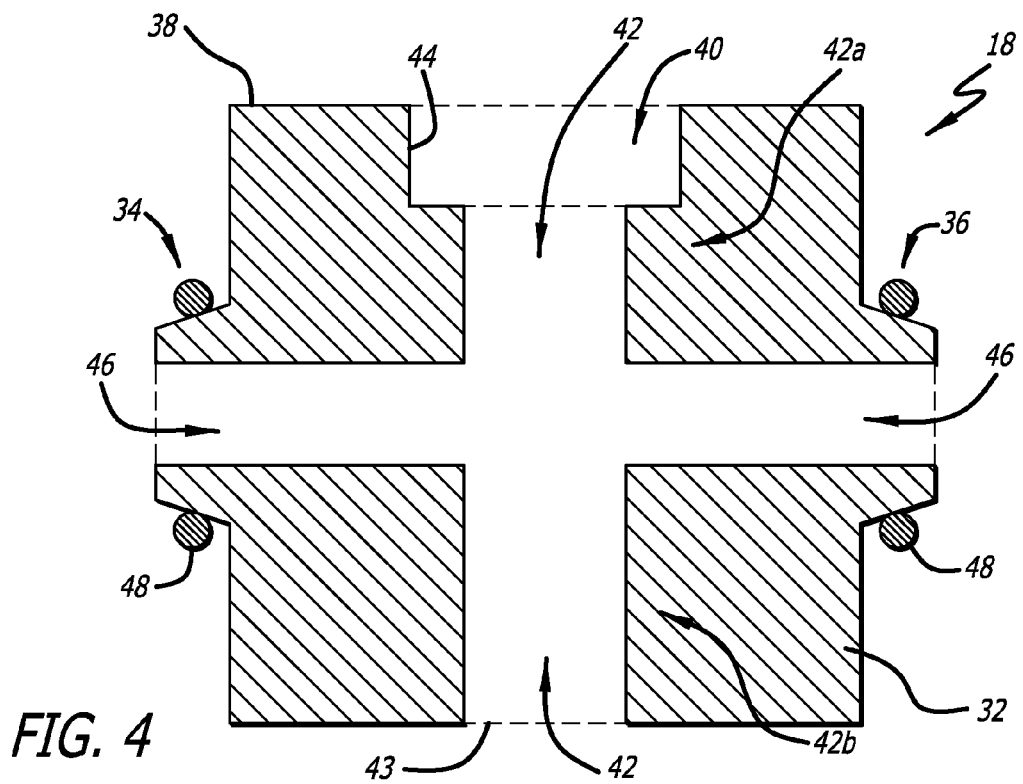
FIG. 4 shows a cross-sectional view of the device body of the present invention.

FIGS. 2 and 4 show the device body 18 of the present invention. As shown, the device body 18 comprises a body member 32 having a first connector receiver 34 and a second connector receiver 36 formed thereon. An interface surface 38 having a receiving aperture 40 is formed on the body member 32. The receiving aperture 40 is sized to sealable receive the sealing flange 22 of the sealing member 16 therein. A pressurizing lumen 42 longitudinally traverses the device body 18 and is in fluid communication with the receiving aperture 40 and the outlet port 43 formed on the body member 32. The pressurizing lumen 42 of the present invention is sized to sealably receive the engagement member 24 of the sealing member 16 therein. The first and second connector receivers 34, 36 are in fluid communication with a monitoring lumen 46 formed within the device body 18. As shown, the monitoring passage 46 intersects and is in fluid communication with the pressurizing lumen 42, effectively bifurcating the pressurizing lumen 42 and forming a first passage 42a and a second passage 42b.

Figure 5:
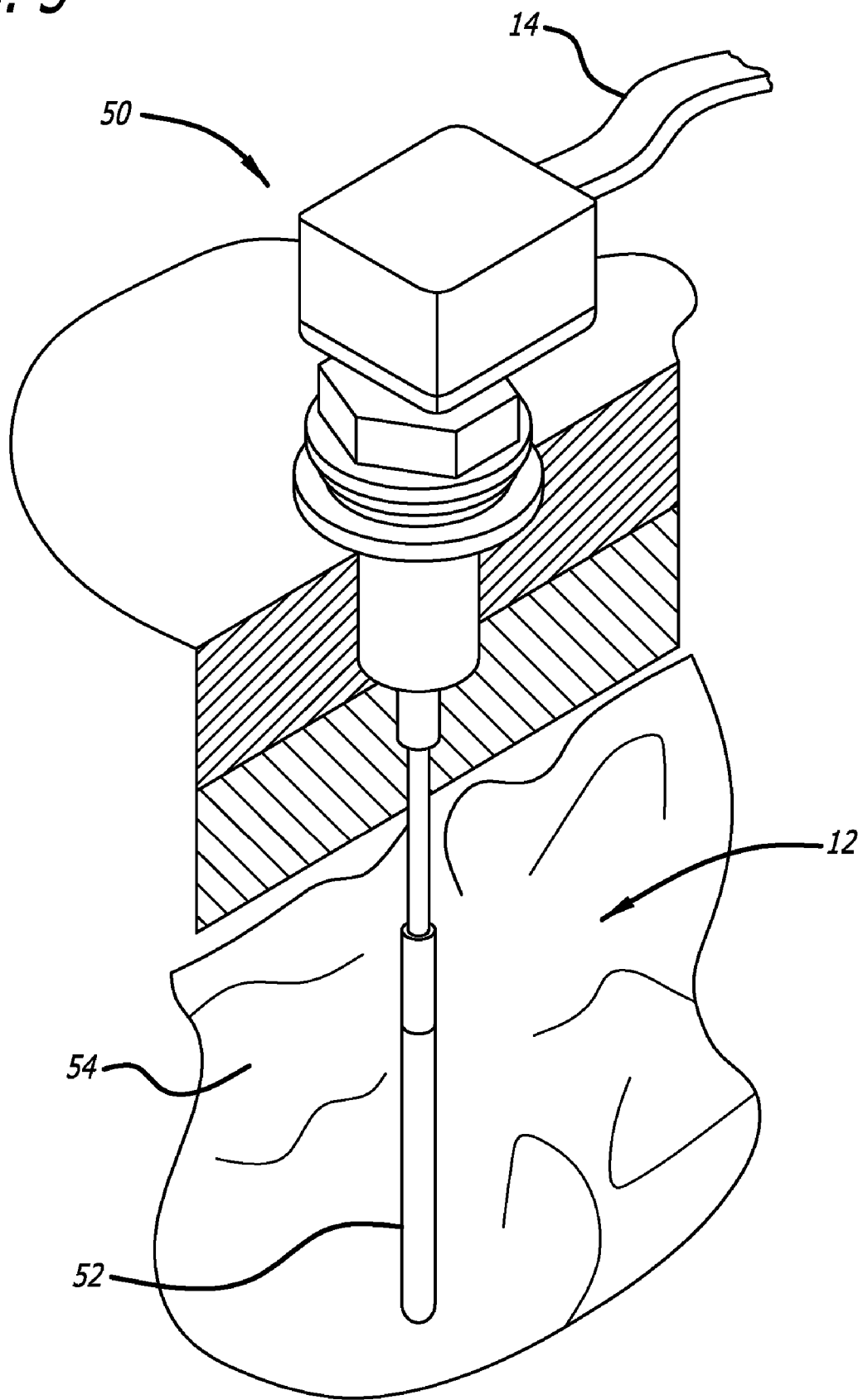
FIG. 5 shows a perspective view of a gas column pressure monitoring catheter.
Figure 6:
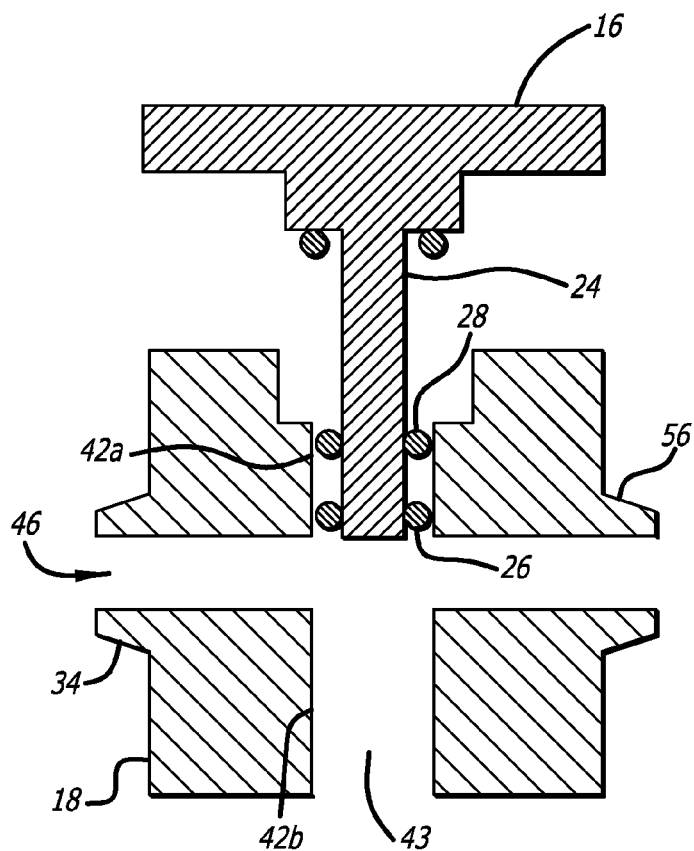
FIG. 6 shows a cross-sectional view of the present invention during use.
Figure 7:
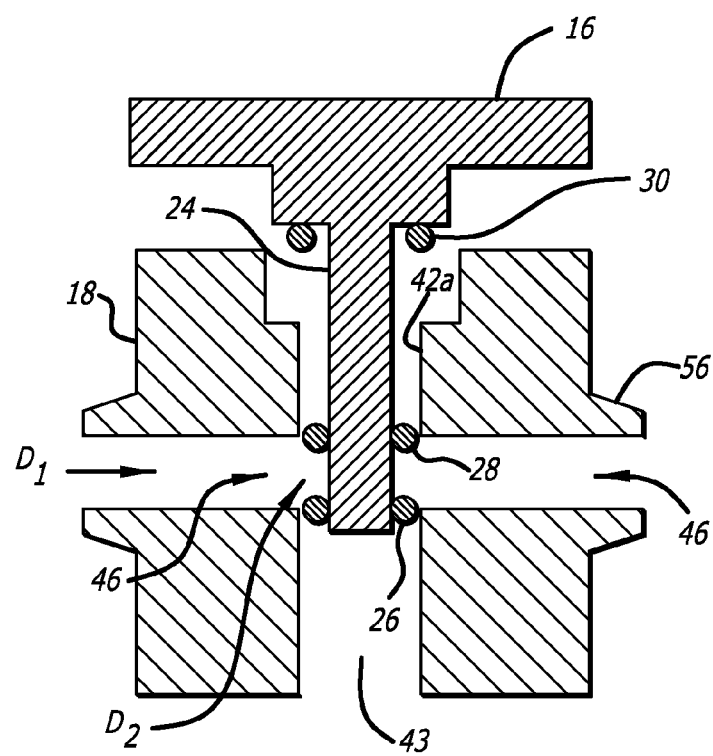
FIG. 7 shows a cross-sectional view of the present invention during use.
Figure 8:
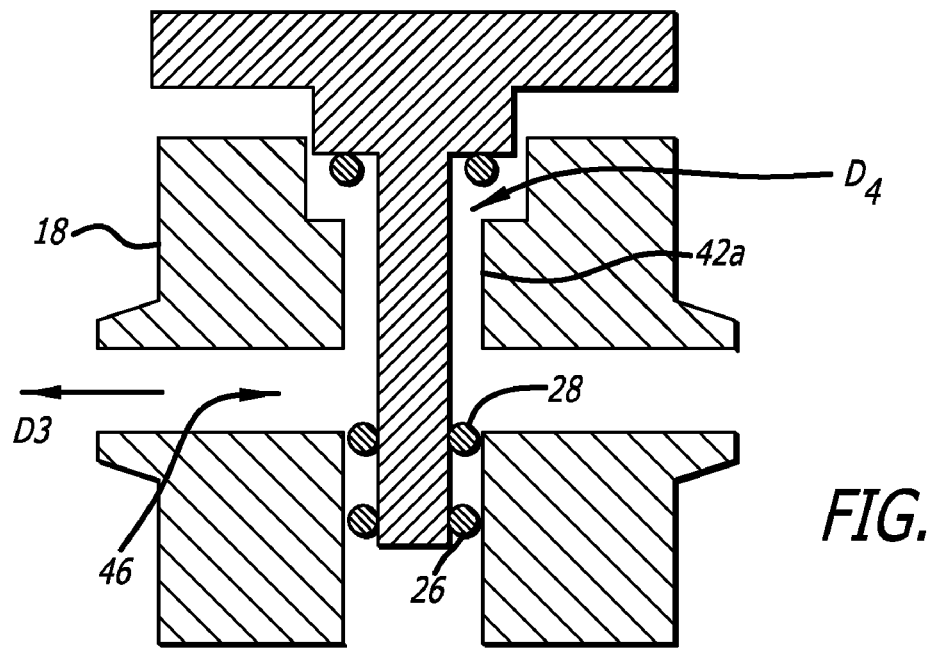
FIG. 8 shows a cross-sectional view of the present invention during use.
Figure 9:
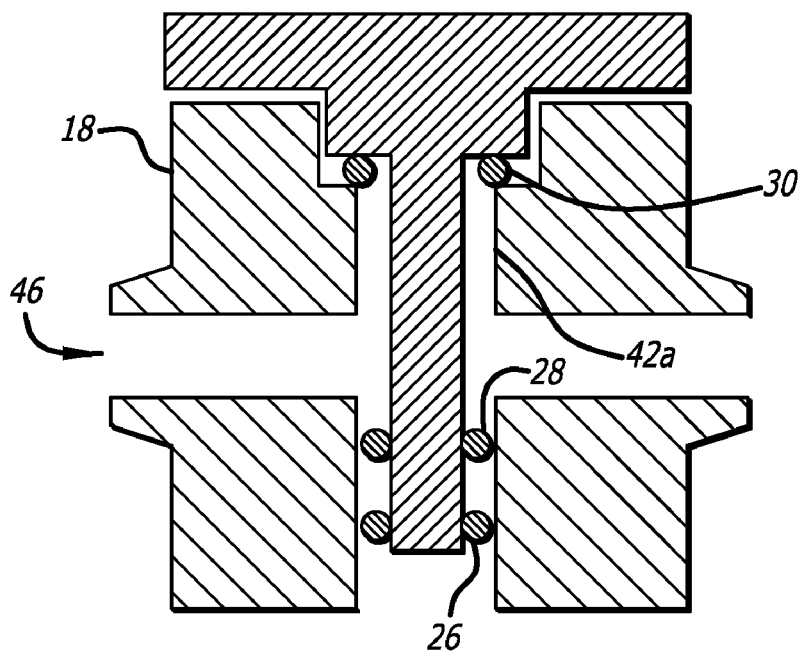
FIG. 9 shows a cross-sectional view of the present invention during use.

The present application further discloses a method of using the pressure monitoring connector 10 in conjunction with a gas column pressure monitoring device. FIGS. 5-9 show the device of the present invention during various stages of use. FIG. 5 show an exemplary gas column pressure monitor 50 in communication with a catheter 12. The bladder 52 of the exemplary gas column pressure monitor 50 is positioned within a tissue media 54. In accordance with Boyle's Law, the bladder 52 of the gas column pressure monitor 50 is in equilibrium with the surrounding tissue media 54. For clarity FIGS. 6-9 show various cross sectional views of the device not coupled to a catheter or a transducer conduit. It should be understood a catheter 12 is attached to a gas column pressure monitor 50 and a transducer conduit 14 is attached to a transducer (not shown). The catheter 12 and the transducer conduit 14 are attached to first and second connector receivers 34, 36 during use. Thereafter, the user inserts the engagement member 24 into the first portion 42a of the pressurizing lumen 42 formed in the device body 18. As shown in FIG. 6, during the initial stages of insertion the monitoring lumen is in communication with the outlet port 43 thereby maintaining the equilibrium between the bladder 52 and tissue media 54 (See FIG. 5). FIG. 7 shows the continued actuation of the present invention wherein the distal portion of the engagement member 24 has traversed the monitoring lumen 46. The first O-ring sealably engages the walls of the second portion 42b of the pressurizing lumen 42 thereby isolating the bladder 52 (see FIG. 5) from the outlet port 43. Furthermore, FIG. 7 illustrates the continued insertion of the engagement member 24 into the device body 18 thereby generating a vacuum D1, D2 within the monitoring lumen 46. As a result, fluid is withdrawn from the bladder 52. As shown in FIG. 8, the continued insertion of the engagement member 24 results in the second O-ring 28 traversing the monitoring lumen 46. Furthermore, the bladder 52 is capable of communicating with the atmosphere through the first portion 42b of the pressurizing lumen 42 and permits the bladder 52 to return to a state of equilibrium D3, D4 with the tissue media 54. FIG. 9 shows engagement member 24 completely inserted in the pressurizing lumen 42 wherein the sealing O-ring 30 has engaged the receiving aperture 40. Those skilled in the art will appreciate that the present invention permits a user to simultaneously attach and equilibrate a gas column pressure monitoring device or other pressure monitoring device to a pressure transducer. Furthermore, it will be appreciated that the present invention reduces or eliminates the possibility a bladder may be over inflated while connecting the pressure monitoring device to a pressure transducer.

Figure 10:
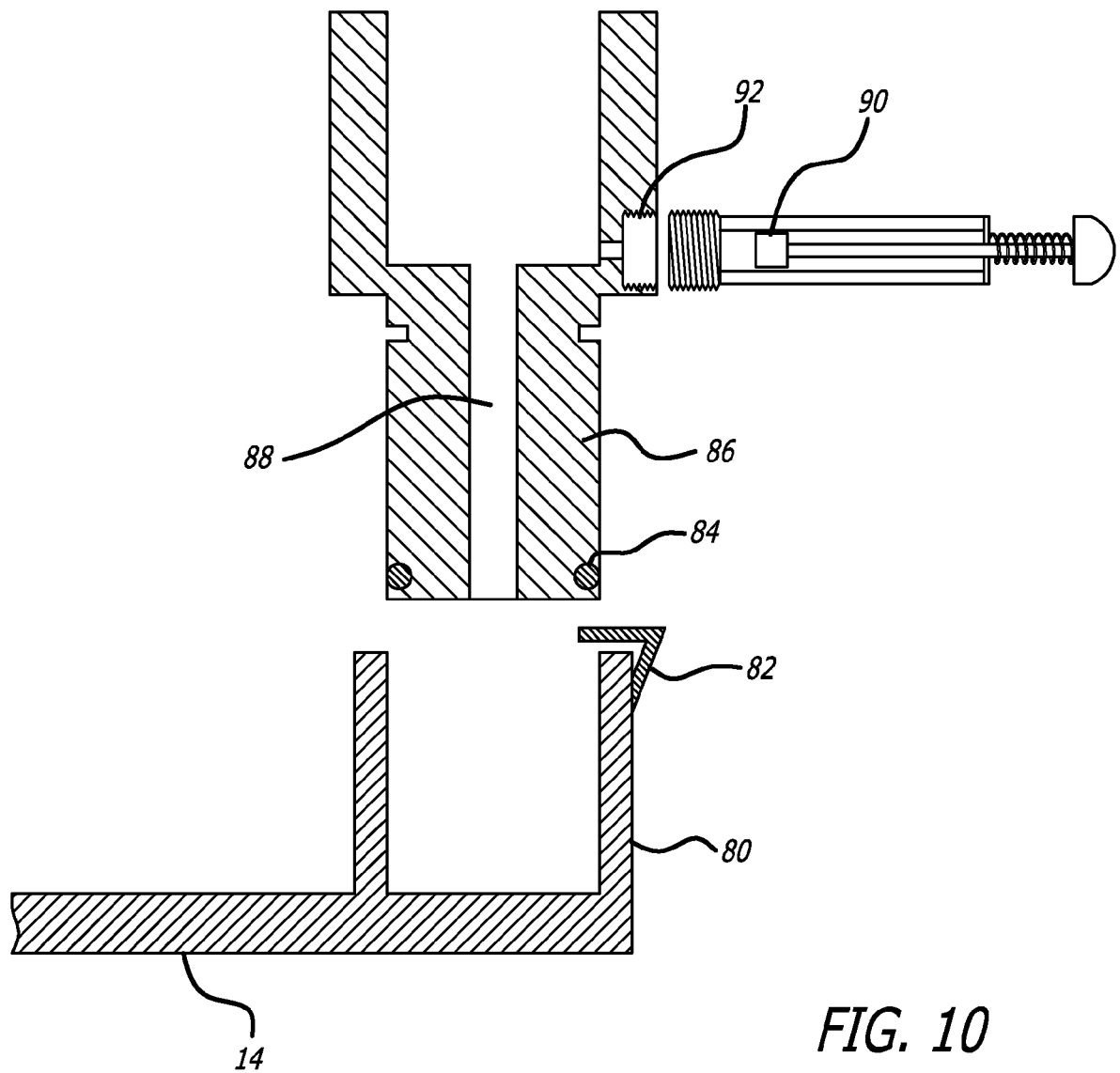
FIG. 10 shows a transducer insert of the present invention.

In an alternate embodiment of the present invention, a transducer insert may be position proximate to a pressure transducer. FIG. 10 illustrates a transducer insert 86 that may be attached to the transducer 80. The transducer insert may be locked into position by a snap-in connector 82. The transducer insert 86 is sealing engaged with the transducer by an O-ring 84. The transducer insert 86 includes a lumen 88 which is in communication with a luer opening 92. The opening 92 is capable of engaging a syringe 90. When the transducer insert 86 attached to the transducer 80, the tranducer insert is in communication with the pressure monitoring catheter. As the plunger of the syringe 90 is withdrawn, a volume of air from the pressure monitoring catheter (not shown) is concomitantly withdrawn. Conversely, the plunger of the syringe may be depressed thereby adding air to the pressure monitoring catheter.

In closing, it is understood that the embodiments of the invention disclosed herein are illustrative of the principals of the invention. Other modifications may be employed which are within the scope of the present invention. Accordingly, the present invention is not limited to that precisely as shown and described in the present disclosure.

What is claimed is:

1. A method of connecting a pressure monitoring catheter to a pressure transducer, comprising:

providing a pressure monitoring connector having an outlet port open to the atmosphere;

coupling a pressure monitoring catheter to said connector;

coupling a transducer to said connector;

adjusting a sealing member in said pressure monitoring connector after coupling said pressure monitoring catheter and said transducer to said connector so as to selectively vent said outlet port to the atmosphere in a first position of said sealing member and to both seal said outlet port and to displace a predetermined volume of air into a passage between said pressure monitoring device and said transducer in a second position of said sealing member, thereby limiting a pressure differential within said pressure monitoring catheter.

2. The method of claim 1, wherein said adjusting a sealing member further comprises moving a plurality of o-rings disposed on said sealing member.

3. The method of claim 1, wherein said coupling a transducer to said connector further comprises coupling said transducer for measuring pressure within a cranium.

4. The method of claim 1, wherein said adjusting a sealing member includes moving said sealing member relative to a body of said pressure monitoring connector.

5. The method of claim 4, wherein said moving said sealing member relative to a body of said pressure monitoring connector further comprises moving said sealing member in a passage of said body of said pressure monitoring connector.

6. The method of claim 5, wherein said outlet port open to the atmosphere is connected to said passage of said body.

7. The method of claim 1, wherein said providing a pressure monitoring connector having an outlet port open to the atmosphere further comprises providing said connector further including a first passage and a second passage.

8. The method of claim 7, wherein said coupling a pressure monitoring catheter to said connector further comprises connecting said first passage to said pressure monitor.

9. The method of claim 8, wherein said coupling a transducer to said connector further comprises connecting said transducer to said first passage.

10. The method of claim 9, wherein said providing said connector further including a first passage and a second passage further comprises providing said first passage intersected by said second passage.

11. The method of claim 10, wherein said providing said connector further comprises providing said second passage connected to said outlet port.

* * * * *